United States Patent [19]

Tour et al.

[11] Patent Number: 5,143,993

[45] Date of Patent: Sep. 1, 1992

[54] SILANE COMPOUND FOR USE IN THE SYNTHESIS OF SEMICONDUCTING POLYMERS WITH PERPENDICULARLY ARRANGED CORES AND METHOD OF SYNTHESIZING SAID COMPOUND

[75] Inventors: James M. Tour; Ruilian Wu; Jeffry S. Schumm, all of Columbia, S.C.

[73] Assignee: University of South Carolina, Columbia, S.C.

[21] Appl. No.: 740,319

[22] Filed: Aug. 5, 1991

Related U.S. Application Data

[62] Division of Ser. No. 492,543, Mar. 12, 1990, Pat. No. 5,059,695.

[51] Int. Cl.$^5$ .............................................. C08G 77/06
[52] U.S. Cl. ......................................... 528/15; 528/30; 528/32; 549/4; 556/406
[58] Field of Search ................. 528/30, 15, 32; 549/4; 556/406

[56] References Cited

U.S. PATENT DOCUMENTS

| | | | |
|---|---|---|---|
| 2,238,669 | 4/1941 | Wiley | 556/478 |
| 2,615,033 | 10/1952 | Hersch | 556/406 |
| 2,640,833 | 6/1953 | Di Giorgio | 528/30 |
| 4,281,094 | 7/1981 | Homan et al. | 528/30 |
| 5,059,695 | 10/1991 | Tour et al. | 549/4 |

FOREIGN PATENT DOCUMENTS 437769 7/1974 U.S.S.R. .

OTHER PUBLICATIONS

Tour et al. "Approaches to Orthogonally Fused Conducting Polymers for Molecular Electronics", Journal of the American Chemical Society, 1990, 112, pp. 5662–5663.
Avriam, J. Am. Chem. Soc. 110 (1988) pp. 5687–5692.
Negeshi, J. Am. Chem. Soc. 111 (1989) pp. 3336–3346.
Fagan, J. Am. Chem. Soc. 110 (1988) pp. 2310–2312.
Negeshi, Heterocycles (1982) 18, pp. 117–122.

Primary Examiner—Melvyn I. Marquis
Assistant Examiner—M. W. Glass
Attorney, Agent, or Firm—Brumbaugh, Graves, Donohue & Raymond

[57] ABSTRACT

The stereochemical structure necessary for preparation of perpendicularly arranged cores is provided by a compound of the formula

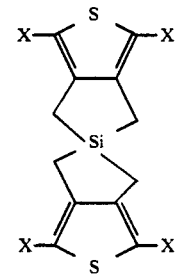

wherein X is a reactive group through which polymeric subunits can be bonded to the compound. In particular, X is advantageously Br. This compound can be synthesized by the reaction of tetrakis(3'-trimethylsilyl-2'-propynyl)silane with zirconocene dichloride and n-butyllithium and adding sulfur monochloride to the reaction product. This produces an adduct in which X is SiMe$_3$. This adduct may be converted to the bromo compound by reaction with bromine. The tetrakis(3'-trimethylsilyl-2'-propynyl)silane may be prepared by forming a magnesium Grignard reagent from 3-bromo-1-trimethylsilylpropyne and reacting the Grignard reagent with silicon tetrachloride.

5 Claims, No Drawings

SILANE COMPOUND FOR USE IN THE SYNTHESIS OF SEMICONDUCTING POLYMERS WITH PERPENDICULARLY ARRANGED CORES AND METHOD OF SYNTHESIZING SAID COMPOUND

The U.S. Government has a paid-up license in this invention and the right in limited circumstances to require the patent owner to license others on reasonable terms as provided for by the terms of Grant No. N00014-89-J-3062 awarded by the Office of Naval Research.

This application is a division of application Ser. No. 07/492,543, filed on Mar. 12, 1990, now U.S. Pat. No. 5,059,695.

BACKGROUND OF THE INVENTION

This invention relates to a silane compound with a defined physical structure for use in forming semiconducting polymers with perpendicularly arranged cores, and to a method of synthesizing this compound.

Conducting organic and organometallic polymers have attracted much recent scientific interest, since they may play a key role in the construction of modern electronic systems. In simple devices, polymers constructed from simple monomer subunits may be sufficient. As electronic component design becomes more complex and more precise, however, more complex monomer units become required to meet the needs of such systems.

As an example, it has been suggested based on calculations that a polymeric compound of the formula

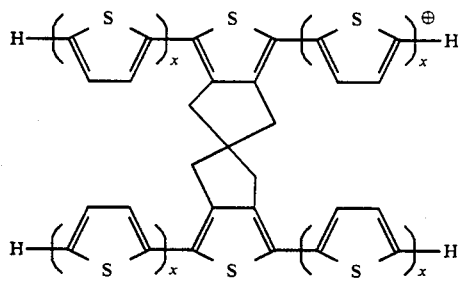

may be suitable for incorporation into future electronic devices. Aviram, A., J. Am. Chem. Soc. 110, 5687 (1988). In this compound, a pro-conducting (non-doped or non-oxidized and hence insulating) polymer is fixed at a 90° angle via a non-conjugated sigma bond network to a conducting (doped or oxidized) polymer. Such a polymeric compound would be useful in memory, logic and amplification computing systems. This compound has not actually been synthesized, however, and thus perpendicularly arranged cores of this type are not actually available.

It is an object of the present invention to provide a molecule which forms the central building block for synthesis of perpendicularly arranged cores.

SUMMARY OF THE INVENTION

In accordance with the invention, the stereochemical structure necessary for preparation of perpendicularly arranged cores is provided by a compound of the formula

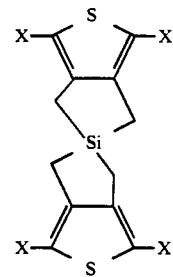

wherein X is a reactive group through which polymeric subunits can be bonded to the compound. In particular, X is advantageously Br or I.

This compound can be synthesized by the method of the invention in which the key step involves the reaction of tetrakis(3'-trimethylsilyl-2'-propynyl)silane

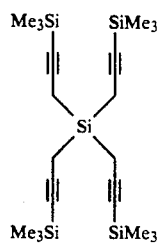

with zirconocene dichloride and n-buthyllithium and adding sulfur monochloride to the reaction product. This produces an adduct in which X is SiMe₃. This adduct may be converted to the bromo compound by reaction with bromine. The tetrakis(3'-trimethylsilyl-2'-propynyl)silane may be prepared by forming a magnesium Grignard reagent from 3-bromo-1-trimethylsilyl-propyne and reacting the Grignard reagent with silicon tetrachloride.

DETAILED DESCRIPTION OF THE INVENTION

The compound of the invention can be synthesized from

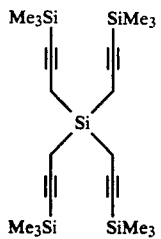

in accordance with the following series of reactions:

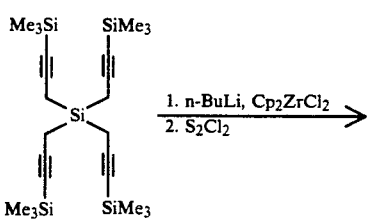

-continued

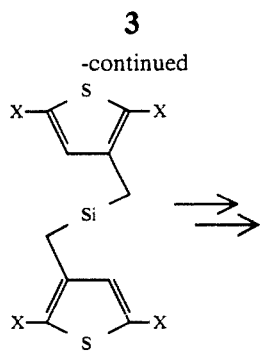

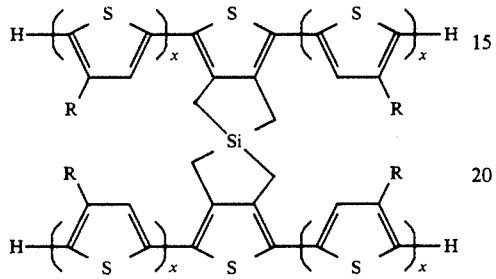

3-Bromo-1-trimethylsilylpropyne for use in the first step can be synthesized by reacting diisopropylamine with n-butyl lithium followed by sequential addition of propargyl bromide and trimethylchlorosilane. Following workup, this procedure yielded 75% of the desired product. Alternatively, this compound can be prepared by reacting propargyl alcohol with n-butyllithium followed by sequential reactions with trimethylchlorosilane, aqueous acid n-butyllithium, p-toluenesulfonyl chloride and lithium bromide. Following workup, this procedure yielded 58.5% of the desired product.

The 3-bromo-1-trimethylsilylpropyne is converted to the magnesium Grignard reagent by reaction with magnesium metal in ether. The Grignard reagent is then reacted with the silicon tetrachloride and worked up to yield tetrakis(3'-trimethylsilyl-2'-propynyl)silane in 90% yield. It should be noted that an analogous coupling reaction intended to give the similar product with a carbon atom in place of the central silicon atom of the compound of the invention, i.e.,

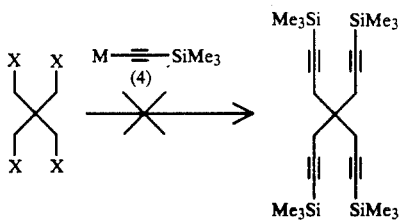

X = I, Br, Cl, OTs   M = MgBr, Li, Al, Zn, Cu
with and without Pd and Ni catalysis was unsuccessful.

The spiro compound of the invention is formed from the tetrakis(3'-trimethylsilyl-2'-propynyl)silane by reaction with zirconocene dichloride and n-butyllithium, followed by addition of sulfur monochloride ($S_2Cl_2$). This reaction produced the compound of the invention, wherein X is $SiMe_3$ with a yield of 41% following workup. A preferred compound of the invention, in which X is Br, can be formed in 88% yield by reacting this compound with bromine. The compound in which X is I can be formed by reacting the trimethylsilyl compound with iodine monochloride (ICl). A compound in which X is OTf ($-O-SO_2-CH_3$) would also be useful, but this compound has not been reached by the present synthetic approach.

The compounds of the invention are intended for use as core structures to define the stereochemistry of perpendicularly arranged polymers. The preparation of such polymers will involve the addition of polymer subunits (monomers or prepolymers) to the core compound of the invention. This can be accomplished, for example, by the following reaction:

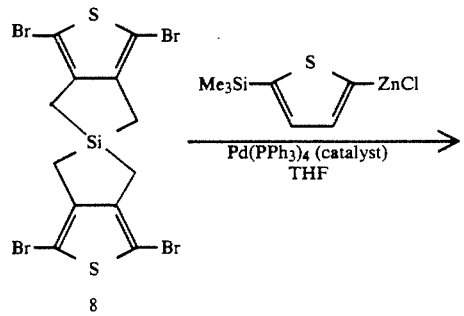

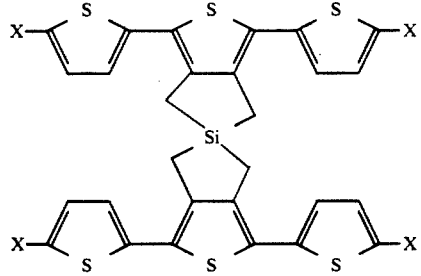

in which additional thiophene moieties are added to each of the bromine groups on the core compound. The reaction conditions, in which 2-bromo-5-(trimethylsilyl)thiophene is added using palladium tetrakis(triphenylphosphine) as a catalyst, are similar to those described by Negishi et al., Heterocycles 18, 117 (1982). The product can be further extended by reconverting the $SiMe_3$ groups to bromo groups by reaction with bromine (in a manner analogous to the bromination of the core compound) and again reacting the bromo compound with 2-bromo-5-(trimethylsilyl)thiophene.

Experimental Procedures

3-Bromo-1-trimethylsilylpropyne was prepared by two methods. Method A: Diisopropylamine (6.1 g, 8.4 mL, 60 mmol) was added over a few min to a solution of n-butyllithium (3.8 g, 23 mL, 60 mmol, 2.6M in hexanes) in ether (65 mL) at −78° C. The obtained solution was cooled to −80° C. to −90° C. and propargyl bromide (5.9 g, 3.8 mL, 50 mmol) was added dropwise over 5 min while keeping the temperature between −75° C. and −80° C. After an additional 5 min at −80° C. trimethylchlorosilane was added between −80° C. and −90° C. Subsequently, a mixture of dry HMPA (7.5 mL) and ether (7.5 mL) was added dropwise with vigorous stirring while carefully keeping the temperature within this range. After this addition, the cooling bath was occasionally removed and the temperature was allowed to rise gradually over 30 min to −40° C., and then to 10° C. The resulting white suspension was poured into 3N aqueous hydrochloric acid (500 mL) and the product was extracted with ether. The combined organic phase was dried over anhydrous sodium sulfate and the solvent was distilled through a vigreux column. The residue was distilled at 72°–74° C./25 mm Hg to afford 7.17 g (75%) of the desired product.

Method B: To propargyl alcohol (28.0 g, 29.0 mL, 0.50 mol) in THF (1 L) was added n-butyllithium (67.3 g, 584 mL, 1.05 mol, 1.8M in hexanes) dropwise by a dropping funnel while maintaining the internal temperature below −60° C. and stirring was continued at this temperature for 0.5 h. Trimethylchlorosilane (114 g, 133 mL, 1.05 mol) was added dropwise by dropping funnel and the mixture was allowed to warm to room temperature and stirred for 0.5 h. Hydrochloric acid (3N, 600 mL) was added and the solution was stirred vigorously for 1 h to hydrolize the silyl ether. The mixture was then poured into water and extracted with ether (3×100 mL). The combined organic phase was washed with sodium bicarbonate and brine, then dried over sodium sulfate. The solvent was removed by distillation through a vigreux column until the volume was about 700 mL. The flask was cooled to −78° C. and n-butyllithium (35.2 g, 306 mL, 550 mmol) was added dropwise by a dropping funnel. The mixture was stirred at this temperature for 0.5 h and p-toluenesulfonyl chloride (104.8 g, 550 mmol) in THF (300 mL) was added dropwise by a dropping funnel. The mixture was allowed to warm to room temperature for 1 h then poured into water and extracted with ether (3×100 mL). The combined organic phase was washed with brine and dried over sodium sulfate. The solvent was removed by rotary evaporation. The residue was added to lithium bromide (87.0 g, 1 mol) in acetone (1 L) at room temperature and stirred overnight. The solution was poured into water and extracted with ether (3×100 mL), the combined organic phase was washed with brine and dried over sodium sulfate. The solvent was distilled through vigreux column. The residue was distilled at 62.5°–64.5° C./15 mm Hg to afford 55.88 g (58.5%) of the desired product as a colorless liquid. IR (neat) 2960, 2908, 2185, 1412, 1250, 1205, 1040, 850, 760, 705, 640, 620 cm$^{-1}$, $^1$H NMR (300 MHz, CDCl$_3$)δ 0.15 (s, 9 H), 3.88 (s, 2 H).

The tetrakis(3'-trimethylsilyl-2'-propynyl)silane was prepared as follows. To magnesium turnings (0.26 g, 10.5 mmol) and 10 mL of anhydrous ether in a 100 mL round bottom flask equipped with a reflux condenser and magnetic stirring bar was added 3-bromo-1-trimethylsilylpropyne (1.3 g. 7.0 mmol) in ether (6 mL). The mixture began a spontaneous reflux within 1 or 2 min and an ice bath was used to maintain a mild reflux. When the initially vigorous reaction had subsided, the solution was left to stir at room temperature for 1 h. The resulting Grignard reagent was then transferred via cannula to a 100 mL round bottom flask and was cooled to −78° C. To this solution was slowly added silicon tetrachloride (0.17 g, 0.12 mL, 1.0 mmol). The mixture was allowed to warm to room temperature for 2 h. Water was carefully added to quench the reaction. The aqueous layer was extracted with ether and the combined ether layers were washed with brine, then dried over anhydrous soldium sulfate. The solvent was removed by rotary evaporation. Distillation (200° C./0.1 mm Hg, Kugelrohr) afforded 0.87 g (90%) of the desired compound as a light yellow wax-solid. IR (neat) 2987, 2187, 1251, 845 cm$^{-1}$; $^1$H NMR (300 MHz, CDCl$_3$) δ 1.93 (s, 8 H), 0.12 (s, 36 H); $^{13}$C NMR (20 MHz, CDCl$_3$) δ 102.16 (4 C, alkyne), 84.95 (4 C, alkyne), 2.81 (4 C, —CH$_2$), 0.14 (12 C, SiCH$_3$); MS [M+−CH$_3$]457, [M+-TMS] 399, [M+-TMSCCCH$_2$] 361; Calc'd for C$_{24}$H$_{44}$Si$_5$ 472.2289. Found: 472.2271.

The sprirotetra(trimethylsilyl)dithiophene compound was prepared as follows: To a solution of zirconocene dichloride (0.387 g, 1.15 mmol) in THF (4.5 mL) was slowly added at −78° C. n-BuLi (0.89 mL, 2.3 mmol, 2.8M in hexanes). The mixture was stirred for 1 h and tetrakis(3'-trimethysilyl-2'-propynyl)silane (0.25 g, 0.52 mmol) in THF (2 mL) was added. The reaction mixture was allowed to warm to room temperature and was stirred for 1 h. Sulfur monochloride (0.15 g, 0.088 mL, 1.15 mmol) in hexane (2 mL) was added dropwise from an addition funnel at 0° C. The solution was stirred for 15 min at room temperature before the reaction was quenched with 3N hydrochloric acid and extracted with ether. The ether extracts were washed with saturated sodium bicarbonate and dried over sodium sulfate. The solvent was removed by rotary evaporation. The residue was purified by flash chromatography (silica gel, hexane) to afford 0.110 g. (41%) of the desired compound as colorless crystals (dec. 198° C.). IR (KBr) 2984, 1395, 1252, 1131, 837 cm$^{-1}$; $^1$H NMR (300 MHz, CDCl$_3$) δ 2.13 (s, 8 H), 0.32 (s, 36 H); $^{13}$C NMR (75 MHz, CDCl$_3$) δ 152.62, 136.81, 15.59, −0.24; Calc'd for C$_{24}$H$_{44}$S$_2$Si$_5$: 536.1731. Found: 536.1739.

The sprirotetra(bromo)dithiophene compound was formed by bromination of this product. To a solution of the above-prepared silane (0.412 g. 0.767 mmol) in carbon tetrachloride (5.0 mL) was slowly added bromine (0.488 g, 0.156 mL, 3.068 mmol) at 0° C. The mixture was allowed to warm to room temperature and stirred for 40 min before quenching with water. The aqueous layer was extracted with methylene chloride (4×10 mL) and the organic layer was washed with brine and dried over sodium sulfate. The solvent was removed by rotatory evaporator and the product was recrystallized from methylene chloride to afford 0.382 g (88%) of the desired compound. IR (KBr) 1548, 1383, 1309, 1139, 965, 930, 872 cm$^{-1}$; $^1$H NMR (300 MHz, CDCl$_3$) δ 2.08 (s, 8 H); $^{13}$C NMR (75 MHz, CDCl$_3$) δ 143.71, 106.06, 16.49. Calc'd for C$_{12}$H$_8$Br$_4$S$_2$Si 561.6550. Found: 561.6567. Anal. Calcd for C$_{12}$H$_8$Br$_4$S$_2$Si; C, 25.55; H, 1.43. Found: C, 25.43, 25.35; H, 1.41, 1.45

Synthesis of the spirotetrasilane can be carried out as follows: To a solution of 2-bromo-5(trimethysilyl)thiophene (1.88 g, 8.0 mmol) in anhydrous ether (15 mL) was slowly added t-butyllithium (1.02 g. 9.41 mL, 16 mmol, 1.7M in pentane) by syringe pump (0.20 mL/min) at −78° C. The solution was stirred at −78° C. for 1 h and transferred via cannula into a solution of anhydrous zinc chloride (1.53 g, 11.2 mmol) in THF (10 mL) and the mixture was stirred at room temperature for 1 h. To a solution of the spiro bromide 8 (0.282 g, 0.5 mmol) and palladium tetrakis(triphenylphosphine) (0.115 g, 0.1 mmol) in THF (4 mL) was added the zinc reagent via cannula and the mixture was stirred at room temperature for 1 h followed by heating to 60° C. for 60 h. The solution was poured into water and extracted with dichloromethane. The combined organic layer was washed with brine, dried over sodium sulfate, filtered through an alumina column to remove the palladium residue, and the solvent was removed by rotary evaporation. The residue was dissolved in hexane and was chromatographed (silica gel, hexane) to give 57 mg of the desired compound as a green crystals (13%). $^1$H NMR (300 mHz, CDCl$_3$) δ 7.27 (d, J=3.52 Hz, 4 H), 7.15 (d, J=3.50 Hz, 4 H), 2.34 (s, 8H), 0.31 (s, 36 H); $^{13}$C NMR (20 MHz, CDCl$_3$) δ 142.51, 140.75, 139.58, 134.34, 128.80, 125.10, 16.64, −0.08.

We claim:

1. A method of preparing a compound of the formula

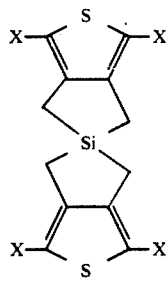

wherein X is a reactive group through which polymeric subunits can be bonded to the compound, comprising the steps of
   (a) reacting tetrakis(3'-trimethylsilyl-2''-propynyl)silane with zirconocene dichloride and n-butyl lithium;
   (b) adding sulfur monochloride to the reaction product of step (a), whereby a compound wherein X is SiMe$_3$ is formed; and
   (c) optionally reacting the compound wherein X is SiMe$_3$ with reagents to convert X to other reactive groups.

2. A method according to claim 1, further comprising the steps of forming a magnesium Grignard reagent from 3-bromo-1-trimethylsilylpropyne and reacting the Grignard reagent with silicon tetrachloride, whereby tetrakis(3'-trimethylsilyl-2'-propynyl)silane for use in step (a) is formed.

3. A method according to claim 1, wherein the compound wherein X is SiMe$_3$ is reacted with bromine, whereby the compound wherein X is Br is formed.

4. A method of forming perpendicular polymers, comprising the step of reacting a compound of the formula

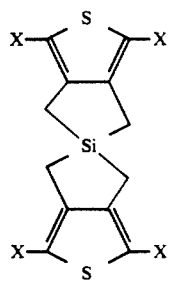

with 2-bromo-5-(trimethylsilyl)-Y using palladium tetrakis(triphenylphosphine) as a catalyst, wherein X is a reactive group through which polymeric subunits can be bonded to the compound and Y is a polymer subunit.

5. A method according to claim 4, wherein X is Br and Y is thiophene.

* * * * *